(12) United States Patent
Takahashi et al.

(10) Patent No.: US 10,369,062 B2
(45) Date of Patent: Aug. 6, 2019

(54) NONWOVEN FABRIC LAMINATE AND ABSORBENT ARTICLE HAVING NONWOVEN FABRIC LAMINATE

(71) Applicant: LIVEDO CORPORATION, Ehime (JP)

(72) Inventors: Yuki Takahashi, Tokushima (JP); Kenji Nakaoka, Osaka (JP)

(73) Assignee: LIVEDO CORPORATION, Ehime (JP)

( * ) Notice: Subject to any disclaimer, the term of this patent is extended or adjusted under 35 U.S.C. 154(b) by 741 days.

(21) Appl. No.: 14/917,062

(22) PCT Filed: Sep. 26, 2014

(86) PCT No.: PCT/JP2014/075563
§ 371 (c)(1),
(2) Date: Mar. 7, 2016

(87) PCT Pub. No.: WO2015/046401
PCT Pub. Date: Apr. 2, 2015

(65) Prior Publication Data
US 2016/0213532 A1    Jul. 28, 2016

(30) Foreign Application Priority Data

Sep. 30, 2013    (JP) ................................. 2013-203774

(51) Int. Cl.
*A61F 13/15*    (2006.01)
*A61F 13/538*    (2006.01)
(Continued)

(52) U.S. Cl.
CPC ...... *A61F 13/538* (2013.01); *A61F 13/49019* (2013.01); *A61F 13/51476* (2013.01);
(Continued)

(58) Field of Classification Search
CPC .......... A61F 13/51476; A61F 13/51478; A61F 13/15699; A61F 13/15731;
(Continued)

(56) References Cited

U.S. PATENT DOCUMENTS 4,720,415 A    1/1988    Vander Wielen et al.
5,455,110 A    10/1995    Connor
(Continued)

FOREIGN PATENT DOCUMENTS

CN    1655748    8/2005
JP    52-42916    10/1977
(Continued)

OTHER PUBLICATIONS

International Search Report dated Dec. 22, 2014 in International (PCT) Application No. PCT/JP2014/075563.
(Continued)

*Primary Examiner* — Jacqueline F Stephens
(74) *Attorney, Agent, or Firm* — Wenderoth, Lind & Ponack, L.L.P.

(57) ABSTRACT

An absorbent article comprising an exterior sheet formed of a nonwoven fabric laminate (1) in which a first nonwoven fabric layer (2), a second nonwoven fabric layer (3) and a third nonwoven fabric layer (4) are laminated from the outer side, wherein the first nonwoven fabric layer (2) and the second nonwoven fabric layer (3) are joined to each other at first joining parts (6), the second nonwoven fabric layer (3) and the third nonwoven fabric layer (4) are joined to each other at second joining parts (7), and a number of the first joining parts is smaller than that of the second joining parts (7).

14 Claims, 6 Drawing Sheets

(51) Int. Cl.
*B32B 5/26* (2006.01)
*D04H 1/559* (2012.01)
*B32B 5/02* (2006.01)
*A61F 13/514* (2006.01)
*A61F 13/49* (2006.01)

(52) U.S. Cl.
CPC ........ *A61F 13/51478* (2013.01); *B32B 5/022* (2013.01); *B32B 5/26* (2013.01); *D04H 1/559* (2013.01); *B32B 2250/03* (2013.01); *B32B 2250/20* (2013.01); *B32B 2307/54* (2013.01); *B32B 2307/724* (2013.01); *B32B 2307/726* (2013.01); *B32B 2555/00* (2013.01)

(58) Field of Classification Search
CPC ..... A61F 13/49009; B32B 5/022; B32B 5/26; B32B 37/06; B32B 37/10; B32B 38/06; B32B 2250/03; B32B 2250/20; B32B 2307/54; B32B 2307/724; B32B 2307/726; B32B 2555/00; B32B 2555/02
See application file for complete search history.

(56) References Cited

U.S. PATENT DOCUMENTS

| | | | |
|---|---|---|---|
| 5,688,157 | A | 11/1997 | Bradley et al. |
| 5,882,769 | A | 3/1999 | McCormack et al. |
| 2002/0026660 | A1 | 3/2002 | Goda |
| 2002/0164465 | A1 | 11/2002 | Curro et al. |
| 2005/0065490 | A1 | 3/2005 | Shimoe et al. |

FOREIGN PATENT DOCUMENTS

| | | |
|---|---|---|
| JP | 62-33889 | 2/1987 |
| JP | 6-255006 | 9/1994 |
| JP | 2002-67199 | 3/2002 |
| JP | 2007-29612 | 2/2007 |
| JP | 2009-207698 | 9/2009 |
| JP | 2009-297096 | 12/2009 |

OTHER PUBLICATIONS

Office Action dated Jul. 19, 2018 in Chinese Application No. 201480047557.9, with English Translation.
Office Action dated Sep. 5, 2018 in Japanese Application No. 2015-539371, with English Translation.
Extended European Search Report dated Mar. 16, 2017 in corresponding European Application No. 14848631.9.
Notice of Reasons for Rejection dated Apr. 2, 2019 in Japanese Application No. 2015-539371, with English Translation.
Second Notification of Office Action dated Apr. 3, 2019 in Chinese Application No. 201480047557.9, with English Translation.

[Fig. 1]
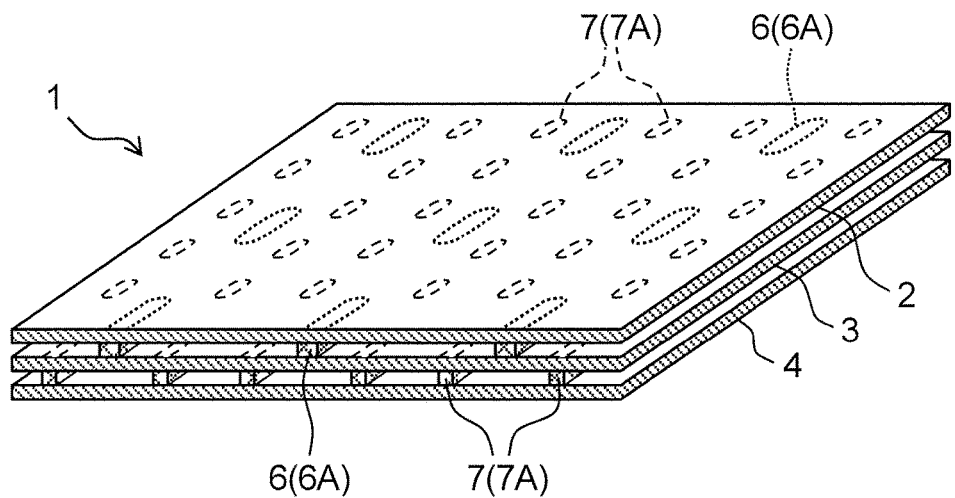
[Fig. 2]
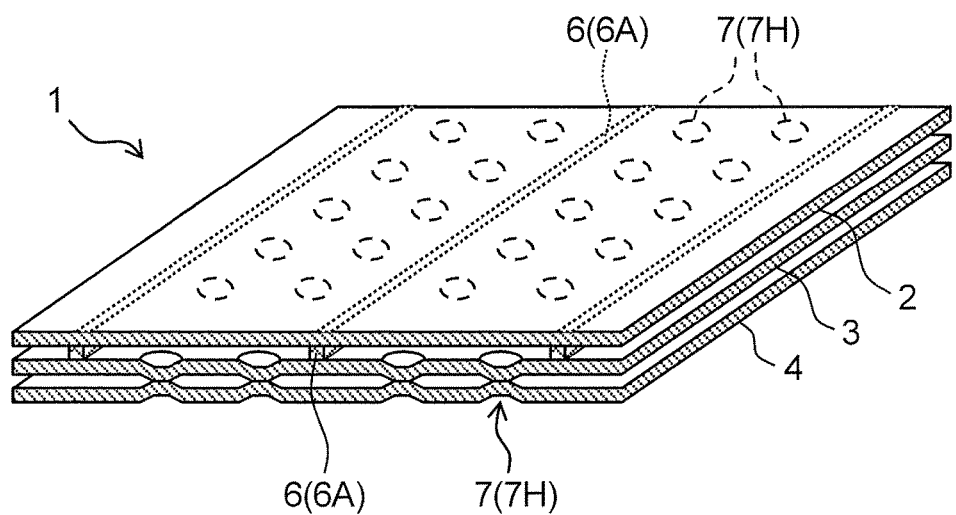

[Fig. 3]
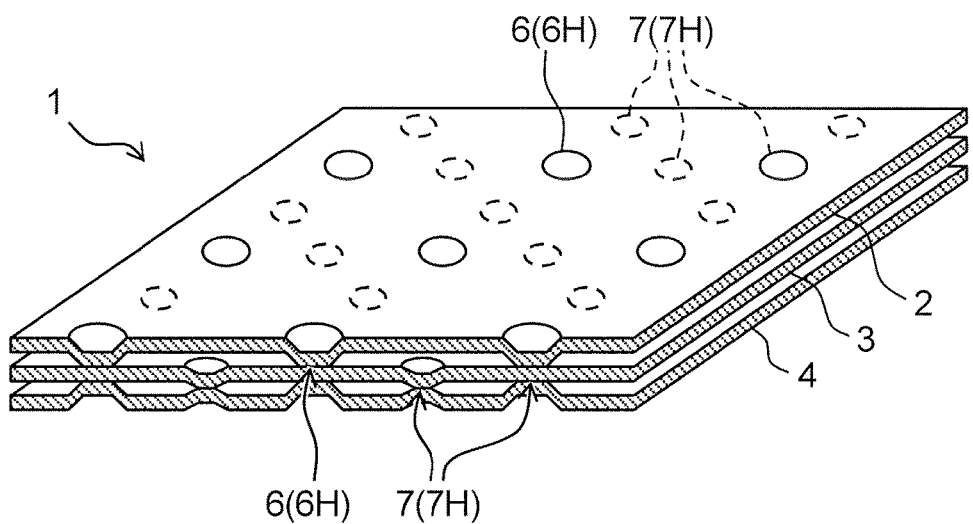
[Fig. 4]
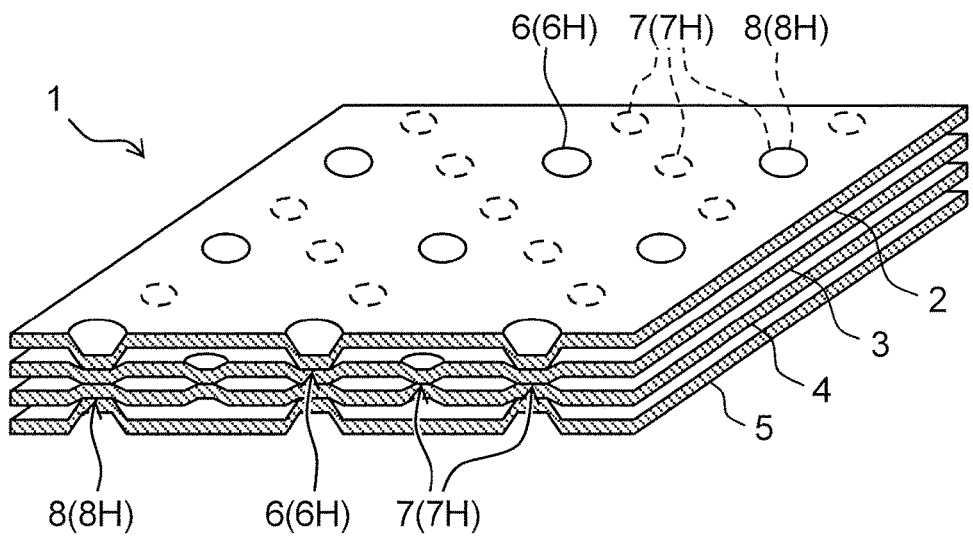

[Fig. 5]
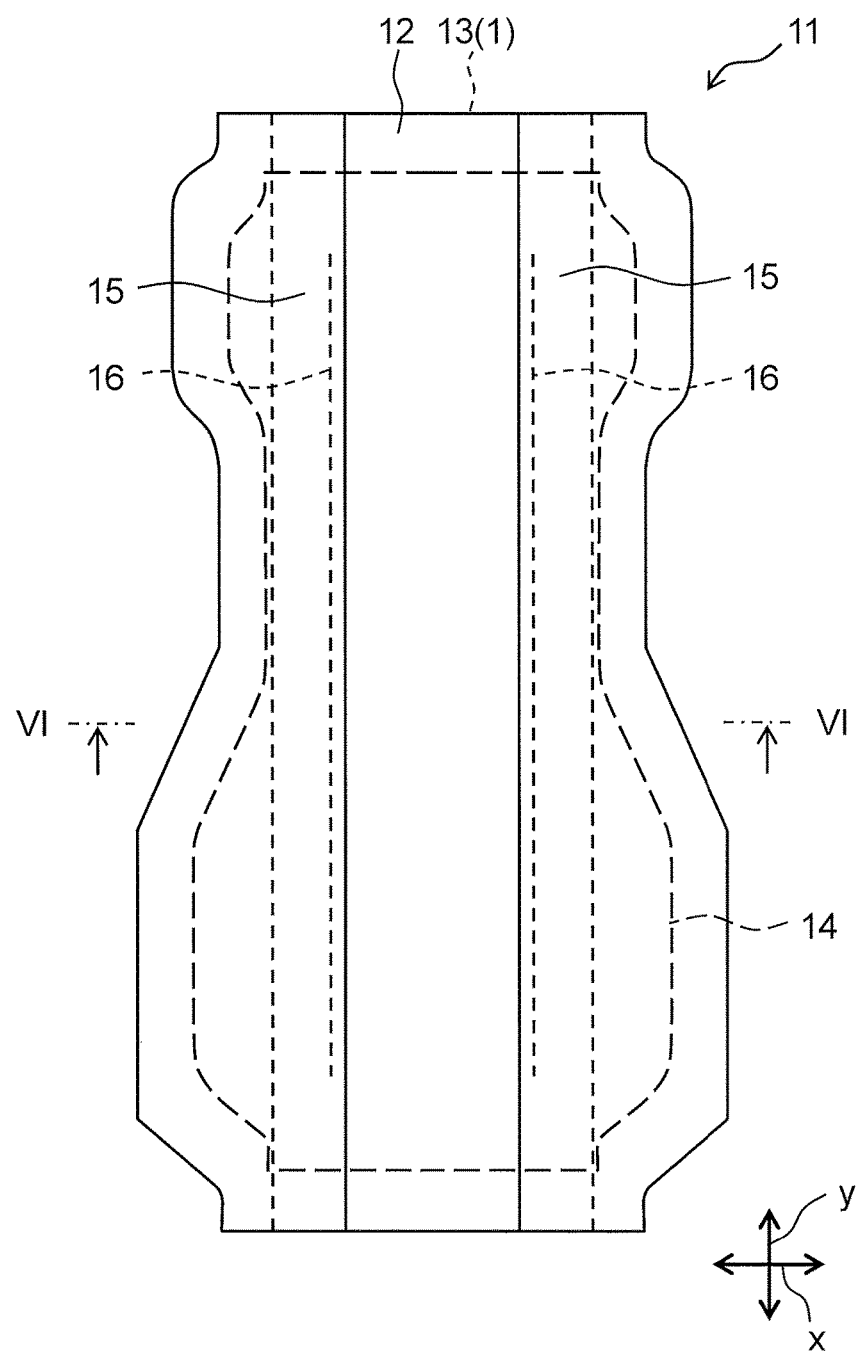

[Fig. 6]
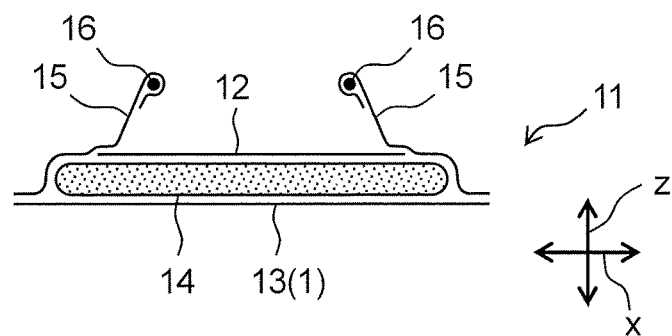
[Fig. 7]
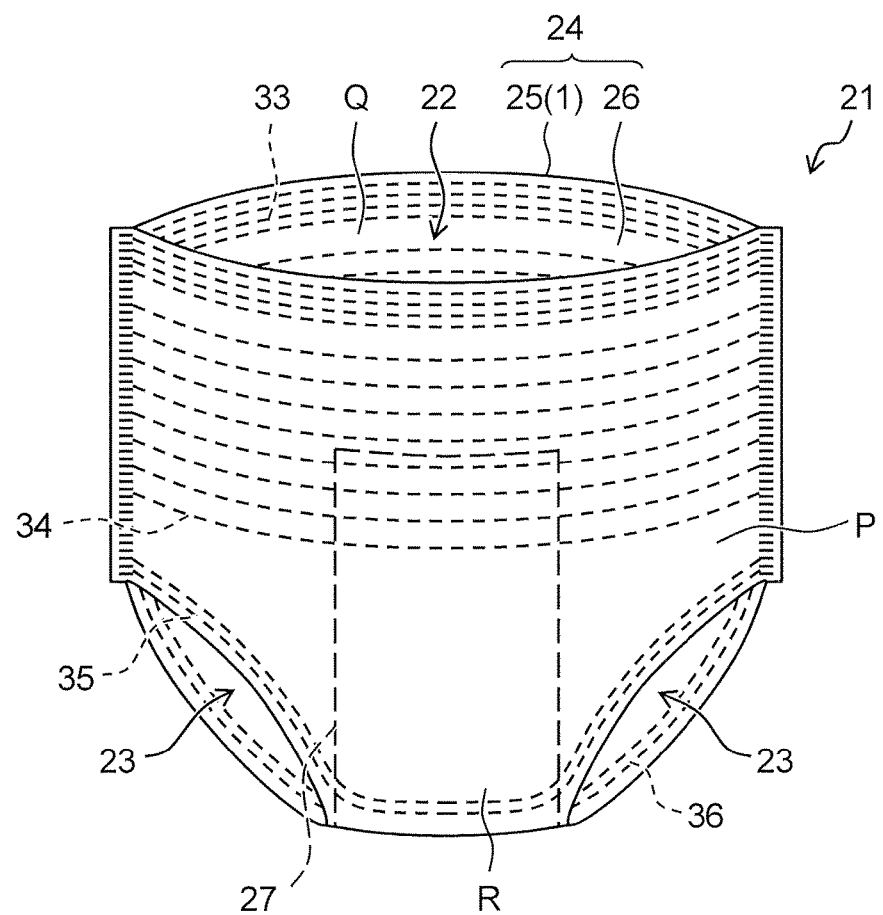

[Fig. 8]
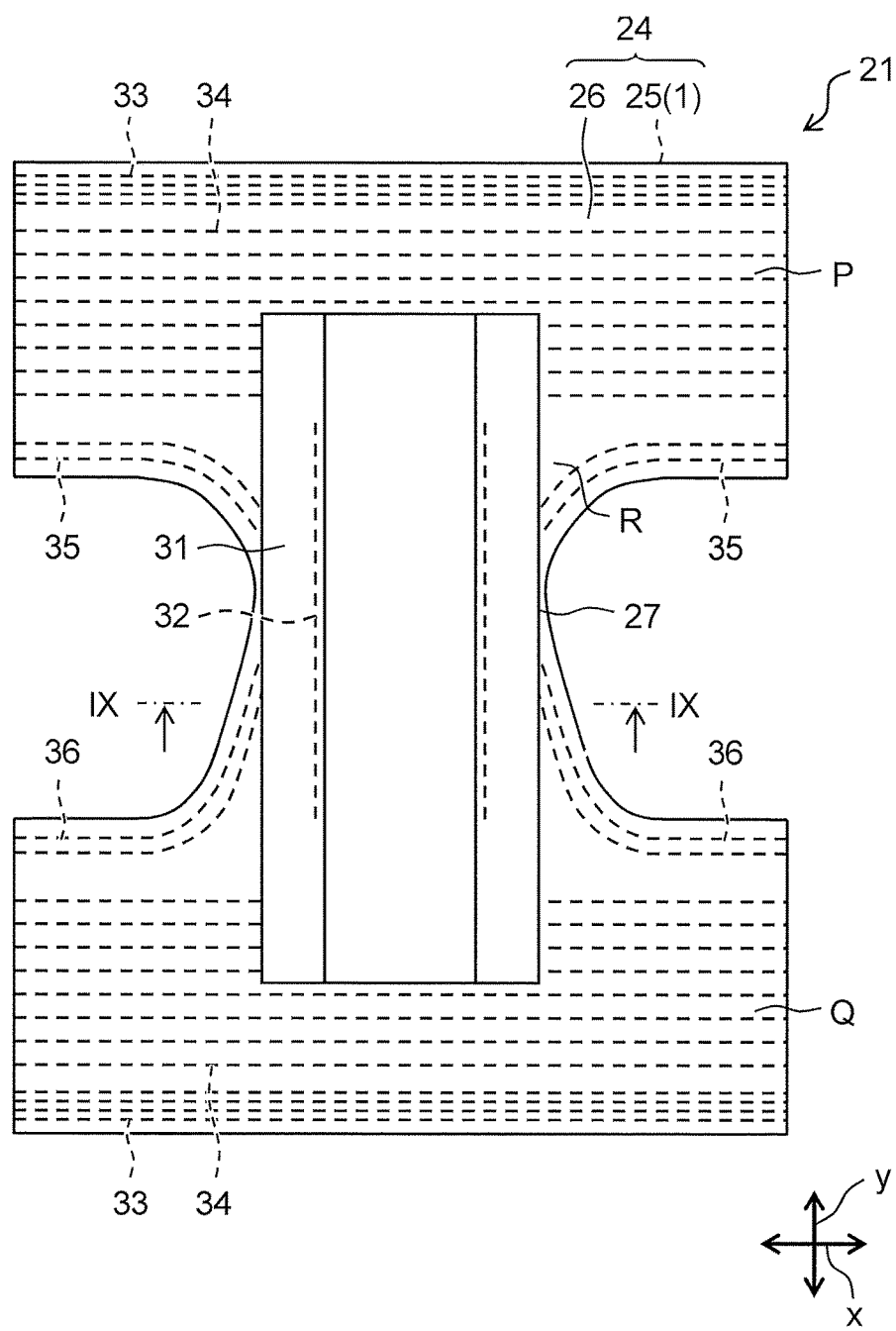

[Fig. 9]
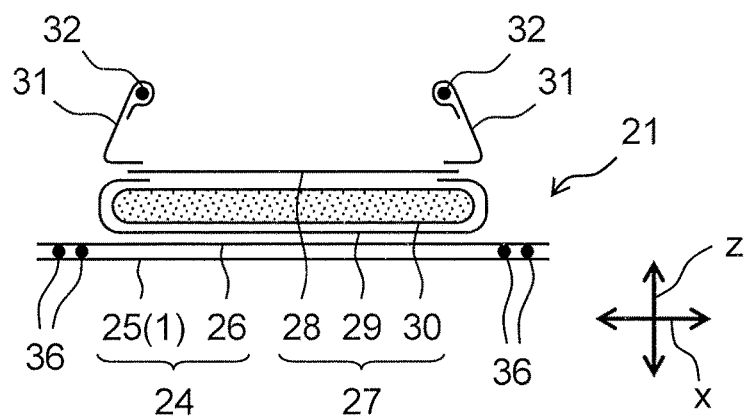

NONWOVEN FABRIC LAMINATE AND ABSORBENT ARTICLE HAVING NONWOVEN FABRIC LAMINATE

TECHNICAL FIELD

The present invention relates to a nonwoven fabric laminate and an absorbent article having the nonwoven fabric laminate such as a disposable diaper, an incontinence pad (including a light incontinence pad) and a sanitary napkin.

BACKGROUND ART

A nonwoven fabric is widely used in life materials and industrial materials, and various kinds of nonwoven fabrics are known. In absorbent articles such as disposable diapers, nonwoven fabrics are widely used as a constituent member thereof, and optimal nonwoven fabrics according to the usage are variously examined. For example, a sheet member disposed on an outer side of an absorbent article (an exterior sheet) is noticeable from an outside of the absorbent article, and hence, it has preferably a good appearance. Also in other applications, nonwoven fabrics preferably have a good appearance. For example, Patent Literature 1 discloses a disposable diaper provided with a sheet member made of a nonwoven fabric of which an outer surface is embossed, and describes that the emboss of the nonwoven fabric suppresses fuzzing.

CITATION LIST

Patent Literature

Patent Literature 1
   Japanese Unexamined Laid-open Patent Application Publication No. 2007-29612

SUMMARY OF INVENTION

Technical Problem

The present invention has been achieved in view of the above circumstances, and the object of the present invention is to provide a nonwoven fabric laminate having a good appearance, and an absorbent article which comprises an exterior sheet provided on an outer side thereof and having a good appearance.

Solution to Problem

A nonwoven fabric laminate of the present invention which solves the above problems is the nonwoven fabric laminate in which a first nonwoven fabric layer, a second nonwoven fabric layer and a third nonwoven fabric layer are laminated in this order, wherein the first nonwoven fabric layer and the second nonwoven fabric layer are joined to each other at first joining parts, the second nonwoven fabric layer and the third nonwoven fabric layer are joined to each other at second joining parts, and a number of the first joining parts is smaller than that of the second joining parts. Since the nonwoven fabric laminate of the present invention is configured in this manner, the first joining parts and the second joining parts are provided in a different pattern from each other, an interlayer distance between the first nonwoven fabric layer and the second nonwoven fabric layer and an interlayer distance between the second nonwoven fabric layer and the third nonwoven fabric layer come to be variously changed. Therefore, degree of transmission or diffusion of light through the nonwoven fabric laminate is made uneven properly, whereby a visual shielding property through the nonwoven fabric laminate can be increased. Further, since the first joining parts formed in the first nonwoven fabric layer are provided smaller in number than the second joining parts which join the second nonwoven fabric layer with the third nonwoven fabric layer, the appearance of the first nonwoven fabric layer side of the nonwoven fabric laminate can be made neat. Therefore, the appearance of the nonwoven fabric laminate is improved seen from the first nonwoven fabric layer side.

It is preferred that a total area of the first joining parts is smaller than that of the second joining parts When the first joining parts are provided in this manner, the first joining parts formed in the first nonwoven fabric layer become small in area and hand feeling of the first nonwoven fabric layer side of the nonwoven fabric laminate can be improved.

It is preferred that both a plurality of the first joining parts and a plurality of the second joining parts are aligned in one direction and another direction in the nonwoven fabric laminate. When the first joining parts and the second joining parts are provided in this manner, the visual shielding property through the nonwoven fabric laminate is increased, thereby improving the appearance thereof.

It is preferred that each of the first nonwoven fabric layer, the second nonwoven fabric layer and the third nonwoven fabric layer is made of a spunbonded nonwoven fabric or an air-through nonwoven fabric. When each of the first nonwoven fabric layer, the second nonwoven fabric layer and the third nonwoven fabric layer is made of a spunbonded nonwoven fabric or an air-through nonwoven fabric, breathability of the nonwoven fabric laminate is increased and internal humidity is easily decreased in the case where the nonwoven fabric laminate is applied to various applications.

The nonwoven fabric laminate of the present invention is preferably applied to an exterior sheet located on an outer side of an absorbent article, whereby a visual shielding property through the exterior sheet is increased and the appearance thereof can be improved. That is, an absorbent article of the present invention comprises an exterior sheet formed of a plurality of nonwoven fabric layers, wherein the exterior sheet is located on an outer side of the absorbent article and has a first nonwoven fabric layer, a second nonwoven fabric layer and a third nonwoven fabric layer from the outer side of the absorbent article, the first nonwoven fabric layer and the second nonwoven fabric layer are joined to each other at first joining parts, the second nonwoven fabric layer and the third nonwoven fabric layer are joined to each other at second joining parts, and a number of the first joining parts is smaller than that of the second joining parts. In the absorbent article of the present invention, since the first joining parts and the second joining parts of the exterior sheet are provided in a different pattern from each other, degree of transmission or diffusion of light through the exterior sheet is made uneven properly, whereby a visual shielding property through the exterior sheet can be increased. Further, since the first joining parts formed in the first nonwoven fabric layer located on an outer side of the exterior sheet are provided smaller in number than the second joining parts which join the second nonwoven fabric layer with the third nonwoven fabric layer, the appearance of the exterior sheet can be made neat. Therefore, the appearance of the absorbent article can be improved.

In the exterior sheet, it is preferred that a total area of the first joining parts is smaller than that of the second joining parts. When the first joining parts are provided in this manner, hand feeling of the exterior sheet can be improved.

It is preferred that both a plurality of the first joining parts and a plurality of the second joining parts are aligned in one direction and another direction in the exterior sheet. When the first joining parts and the second joining parts are provided in this manner, the visual shielding property through the exterior sheet is increased, thereby improving the appearance of the absorbent article.

It is preferred that each of the first nonwoven fabric layer, the second nonwoven fabric layer and the third nonwoven fabric layer is made of a spunbonded nonwoven fabric or an air-through nonwoven fabric. When each of the first nonwoven fabric layer, the second nonwoven fabric layer and the third nonwoven fabric layer is made of a spunbonded nonwoven fabric or an air-through nonwoven fabric, breathability of the exterior sheet is increased and internal humidity is easily decreased in wearing the absorbent article.

In the case that an elastic member is disposed to a skin-facing side of the exterior sheet, it is preferred that the first joining part has a shape that is shorter in an extending direction of the elastic member than in an orthogonal direction thereof. When the first joining part is provided in this manner, many wrinkles extending in a direction orthogonal to the extending direction of the elastic member are easily formed in the exterior sheet, and the elastic member can be made hardly to be seen from the outside of the exterior sheet to improve the appearance of the absorbent article. From the same viewpoint, it is also preferable that a plurality of the first joining parts are aligned in an extending direction of the elastic member and an orthogonal direction thereof, and a distance between the first joining parts in the extending direction is wider than that in the orthogonal direction.

In the case that the absorbent article is a pants-type disposable diaper and an elastic member extending in a width direction of the diaper is disposed at a body circumference part of the diaper between the exterior sheet and an inner sheet provided on a skin-facing side of the exterior sheet, it is preferred that the first joining part has a shape that is longer in a longitudinal direction of the diaper than in the width direction of the diaper. When the first joining part is provided in this manner, many wrinkles extending in the longitudinal direction are formed in the exterior sheet, and the elastic member can be made hardly to be seen from the outside of the exterior sheet to improve the appearance of the diaper. In this case, from the same viewpoint, it is also preferable that a plurality of the first joining parts are aligned in the longitudinal direction of the diaper and the width direction of the diaper, a distance between the first joining parts in the width direction of the diaper is wider than that in the longitudinal direction of the diaper.

Advantageous Effects of Invention

According to the nonwoven fabric laminate of the present invention, since the nonwoven fabric layers are joined to each other in a different pattern from each other, interlayer distances between the nonwoven fabric layers are variously changed, whereby a visual shielding property through the nonwoven fabric laminate can be increased. Further, since the joining parts formed in the first nonwoven fabric layer are provided smaller in number, the appearance of the first nonwoven fabric layer side of the nonwoven fabric laminate can be made neat. Therefore, the appearance of the nonwoven fabric laminate is improved seen from the first nonwoven fabric layer side. Further, according to the absorbent article of the present invention in which the nonwoven fabric laminate of the present invention is used for the exterior sheet, a visual shielding property through the exterior sheet can be increased and the appearance of the exterior sheet can be made neat, and therefore, the appearance of the absorbent article can be improved.

BRIEF DESCRIPTION OF THE DRAWINGS

FIG. 1 shows a perspective view of a nonwoven fabric laminate.

FIG. 2 shows a perspective view of a nonwoven fabric laminate.

FIG. 3 shows a perspective view of a nonwoven fabric laminate.

FIG. 4 shows a perspective view of a nonwoven fabric laminate.

FIG. 5 shows a plan view of a skin-facing side of an incontinence pad as an absorbent article.

FIG. 6 shows a cross-sectional view along a line VI-VI of the incontinence pad shown in FIG. 5.

FIG. 7 shows a perspective view of a pants-type disposable diaper as an absorbent article.

FIG. 8 shows a plan view of the pants-type disposable diaper shown in FIG. 7 in a developed state where a front part and a rear part are disjoined.

FIG. 9 shows a cross-sectional view along a line IX-IX of the pants-type disposable diaper shown in FIG. 8.

DESCRIPTION OF THE PREFERRED EMBODIMENTS

[Nonwoven Fabric Laminate]

A nonwoven fabric laminate of the present invention comprises a plurality of nonwoven fabric layers, wherein the nonwoven fabric layers which are laminated adjacently are joined to each other at joining parts. According to the nonwoven fabric laminate of the present invention, it is possible to increase a visual shielding property and improve the appearance thereof by appropriately providing the joining parts for boding the nonwoven fabric layers to each other.

The nonwoven fabric laminate comprises a first nonwoven fabric layer, a second nonwoven fabric layer and a third nonwoven fabric layer. The first nonwoven fabric layer, the second nonwoven fabric layer and the third nonwoven fabric layer are laminated in this order, and it is preferred that the first nonwoven fabric layer faces outward.

The nonwoven fabric laminate of the present invention can be applied to conventionally-known nonwoven fabric products, that include, for example, absorbent articles such as a disposable diaper and an incontinence pad; covers such as a pillow cover, a shoe cover and a suit cover; bags such as a storage bag; protective clothing such as a protective suit and a surgical gown; and sheets such as a drape, an agricultural sheet, a wet tissue and a wet towel. In the case of applying to absorbent articles, covers, bags and protective clothing, it is preferred that the first nonwoven fabric layer is located on an outer surface thereof, whereby the appearance of the nonwoven fabric products can be improved. In the case of applying to sheets, the first nonwoven fabric layer is preferably located on an outer surface thereof during use, or the nonwoven fabric laminate may be folded so that the first nonwoven fabric layer is located outside.

The nonwoven fabric laminate is formed such that the first nonwoven fabric layer and the second nonwoven fabric layer are joined to each other at first joining parts and the second nonwoven fabric layer and the third nonwoven fabric layer are joined to each other at second joining parts. In the nonwoven fabric laminate, a part where the first nonwoven fabric layer and the second nonwoven fabric layer are joined to each other is the first joining part and a part where the second nonwoven fabric layer and the third nonwoven fabric layer are joined to each other is the second joining part.

In the nonwoven fabric laminate, a number of the first joining parts is smaller than that of the second joining parts. Thus, the second joining parts are provided in high density in a numerical criterion than the first joining parts. The number of the first joining parts is able to be easily determined by counting a number of the first joining parts formed in the first nonwoven fabric layer. The number of the second joining parts is able to be determined by counting a number of the second joining parts formed in the second nonwoven fabric layer or the third nonwoven fabric layer; however, in the case where the third nonwoven fabric layer faces outward, it is convenient to count a number of the second joining parts formed in the third nonwoven fabric layer. The numbers of the first joining parts and the second joining parts may be measured by counting numbers of the first joining parts and the second joining parts formed in a certain area (e.g., an area of 5 cm×5 cm).

Since the nonwoven fabric laminate is configured in the above manner, the first joining parts and the second joining parts are provided in a different pattern from each other, and an interlayer distance between the first nonwoven fabric layer and the second nonwoven fabric layer and an interlayer distance between the second nonwoven fabric layer and the third nonwoven fabric layer are variously changed, that makes degree of transmission or diffusion of light through the nonwoven fabric laminate uneven properly, whereby a visual shielding property through the nonwoven fabric laminate can be increased. Therefore, when the nonwoven fabric laminate of the present invention is applied to the above-described nonwoven fabric products, contents and the like covered by the nonwoven fabric laminate can be properly concealed. Further, since the first joining parts formed in the first nonwoven fabric layer which is located on an outer surface of the nonwoven fabric laminate are provided smaller in number than the second joining parts which join the second nonwoven fabric layer with the third nonwoven fabric layer, the appearance of the first nonwoven fabric layer side of the nonwoven fabric laminate can be made neat. Therefore, the appearance of the nonwoven fabric laminate is improved seen from the first nonwoven fabric layer side. Furthermore, though the first joining parts and the second joining parts are formed by applying an adhesive to the nonwoven fabric layer, thermal-fusion-bonding the nonwoven fabric layers to each other, or the like, and such formed joining parts tend to be hardened to deteriorate the hand feeling, decreasing the number of the first joining parts formed in the first nonwoven fabric layer enables improving the hand feeling of the first nonwoven fabric layer side of the nonwoven fabric laminate.

The first joining part and the second joining part are formed by a conventionally-known bonding means, and may be formed by applying an adhesive to the nonwoven fabric layer, thermal-fusion-bonding the nonwoven fabric layers to each other, or the like, as described above. Thermal-fusion-bonding of the nonwoven fabric layers may be conducted by bringing a heated heat-transfer material contact with the nonwoven fabric layer to melt a part of the nonwoven fabric layer or by bringing a ultrasonic transducer contact with the nonwoven fabric layer to melt a part of the nonwoven fabric layer with ultrasonic vibration, in the state where the nonwoven fabric layers are stacked.

In the present invention, the nonwoven fabric laminate are formed by laminating the first nonwoven fabric layer, the second nonwoven fabric layer and the third nonwoven fabric layer and is handled as a single sheet member. Therefore, in the nonwoven fabric laminate, it is preferred that the second nonwoven fabric layer is provided between the first nonwoven fabric layer and the third nonwoven fabric layer, the second nonwoven fabric layer is provided adjacent to the first nonwoven fabric layer and the third nonwoven fabric layer, and any other member is not provided both between the first nonwoven fabric layer and the second nonwoven fabric layer and between the second nonwoven fabric layer and the third nonwoven fabric layer. In addition, the first nonwoven fabric layer and the second nonwoven fabric layer are not joined to each other overall, and the second nonwoven fabric layer and the third nonwoven fabric layer are not joined to each other overall. Thus, the first nonwoven fabric layer is partly joined to the second nonwoven fabric layer by the first joining parts and the second nonwoven fabric layer is partly joined to the third nonwoven fabric layer by the second joining parts.

The nonwoven fabric laminate may further comprise another layer in addition to the first nonwoven fabric layer, the second nonwoven fabric layer and the third nonwoven fabric layer. The another layer is preferably a nonwoven fabric layer. In the case that the another layer is provided on an outer side of the first nonwoven fabric layer, it is preferred that the plural first nonwoven fabric layers are stacked and the stacked plural first nonwoven fabric layers are joined to each other in the same pattern as the first joining part.

In the nonwoven fabric laminate, a fourth nonwoven fabric layer may be provided outside of the third nonwoven fabric layer. In this case, the first nonwoven fabric layer, the second nonwoven fabric layer, the third nonwoven fabric layer and the fourth nonwoven fabric layer are laminated in this order. In the case that the nonwoven fabric laminate comprises the fourth nonwoven fabric layer, the fourth nonwoven fabric layer and the third nonwoven fabric layer are joined to each other at third joining parts. A part where the third nonwoven fabric layer and the fourth nonwoven fabric layer are joined to each other is the third joining part. In this case, it is preferable that a number of the third joining parts is smaller than that of the second joining parts. When the nonwoven fabric laminate is configured in this manner, the appearance of the nonwoven fabric laminate can be improved seen from both the first nonwoven fabric layer side and the fourth nonwoven fabric layer side. That is, since the first joining parts and the second joining parts are provided in a different pattern from each other and the second joining parts and the third joining parts are provided in a different pattern from each other, interlayer distances between the respective nonwoven fabric layers are variously changed, whereby the visual shielding property through the nonwoven fabric laminate can be improved. Furthermore, since the first joining parts formed in the first nonwoven fabric layer and the third joining parts formed in the fourth nonwoven fabric layer are provided smaller in number than the second joining parts which join the second nonwoven fabric layer with the third nonwoven fabric layer, the appearance of the first nonwoven fabric layer side and the fourth nonwoven fabric layer side of the nonwoven fabric laminate can be made neat.

The third joining part is also formed by a conventionally-known bonding means as described above. The third nonwoven fabric layer and the fourth nonwoven fabric layer are not also joined to each other overall and the third nonwoven fabric layer is partly joined to the fourth nonwoven fabric layer by the third joining part. In addition, it is preferred that any other member is not provided between the third nonwoven fabric layer and the fourth nonwoven fabric layer. The number of the third joining parts is able to be easily determined by counting a number of the third joining parts formed in the fourth nonwoven fabric layer. The number of the third joining parts may be measured by counting a number of the third joining parts formed in a certain area (e.g., an area of 5 cm×5 cm).

It is preferred that a total area of the the first joining parts is smaller than that of the second joining parts. When the first joining parts are provided in this manner, the first joining parts formed in the first nonwoven fabric layer become small in area and hand feeling of the first nonwoven fabric layer side of the nonwoven fabric laminate can be improved. In the case that the nonwoven fabric layer has the third joining part (that is, the nonwoven fabric laminate comprises the fourth nonwoven fabric layer), a total area of the third joining parts is also preferably smaller than that of the second joining parts. When the first and third joining parts are provided in this manner, the first joining parts formed in the first nonwoven fabric layer and the third joining parts become small in area and hand feeling of both the first nonwoven fabric layer side and the fourth nonwoven fabric layer side of the nonwoven fabric laminate can be improved. The area of the each joining part may be measured by counting a total area of the each joining part formed in a certain area (e.g., an area of 5 cm×5 cm).

It is preferable that an area (an average value) of the single first joining part is larger than that of the single second joining part. Thus, it is preferable that the first joining part is disposed in a shape that is larger on average than the second joining part. By providing the first joining part in this manner, joining strength between the first nonwoven fabric layer and the second nonwoven fabric layer is easily ensured even when the first joining parts are provided so as to be smaller in number than the second joining parts. In the case that the nonwoven fabric laminate has the third joining part (that is, the nonwoven fabric laminate comprises the fourth nonwoven fabric layer), it is preferred that an area (an average value) of the single third joining part is larger than that of the single second joining part. Thus, it is preferred that the third joining part is disposed in a shape that is larger on average than the second joining part. By providing the third joining part in this manner, joining strength between the third nonwoven fabric layer and the fourth nonwoven fabric layer is easily ensured even when the third joining parts are provided so as to be smaller in number than the second joining parts.

The third joining part may be disposed in a same pattern as the first joining part or may be disposed in a different pattern from the first joining part. The number of the third joining parts provided in a certain area may be same as that of the first joining parts or may be different from that of the first joining parts. Further, the total area of the third joining parts may be same as that of the first joining parts or may be different from that of the first joining parts, and the area (an average value) of the single third joining part may be same as that of the first joining part or may be different from that of the first joining part.

The total area of the first joining parts and the area of the single first joining part are able to be easily determined by measuring the first joining parts formed in the first nonwoven fabric layer. The total area of the second joining parts and the area of the single second joining part are able to be determined by measuring the second joining parts formed in the second nonwoven fabric layer or the third nonwoven fabric layer; however, in the case that the third nonwoven fabric layer faces outward, it is convenient to measure the second joining parts formed in the third nonwoven fabric layer. The total are of the third joining parts and the area of the single third joining part are able to be determined by measuring the third joining parts formed in the fourth nonwoven fabric layer.

Patterns and arrangements of the respective joining parts are not particularly limited. The respective joining parts may be disposed in a scattered point pattern in any shape or may be disposed in a lattice pattern or a linear pattern. In the case that the first to third joining parts are disposed in a scattered point pattern, each single shape of the first to third joining parts is not particularly limited and may be circular, elliptical, polygonal, wavy, starlike or the other, and these may be provided in a regular pattern or in a random pattern. In the case that the first to third joining parts are disposed in a lattice pattern or a linear pattern, each line constituting the lattice pattern or the linear pattern may be any form such as a straight line, a wavy line, a zigzag line or the like, and in this case, the each line is preferably provided over a substantially entire area of the nonwoven fabric layer in one direction or in both one direction and another direction in the plane. In any case, at least a portion of the second joining parts is preferably provided at a region between the first joining parts, and thus, it is preferably provided that a region where the first joining part is overlapped with a region where the second joining part. In the case where the nonwoven fabric laminate has the third joining part, at least a portion of the second joining parts is preferably provided at a region between the third joining parts, and thus, it is preferably provided that a region where the third joining part is provided is overlapped with the region where the second joining part is provided.

The first joining parts are preferably disposed in a scattered point pattern. When the first joining parts are disposed in a scattered point pattern, hand feeling of the first nonwoven fabric layer side of the nonwoven fabric laminate can be improved. Furthermore, by providing the first joining parts in a scattered point pattern, the first nonwoven fabric layer can be formed so as to float to the second nonwoven fabric layer in more area, thereby improving the visual shielding property through the nonwoven fabric laminate. From the viewpoint of improving the appearance of the nonwoven fabric laminate, it is preferred that a plurality of the first joining parts are aligned in both one direction and another direction in the nonwoven fabric laminate. Here, one direction and another direction in the nonwoven fabric laminate means one direction and another direction in a plane including the nonwoven fabric laminate.

The second joining parts are preferably disposed in a scattered point pattern. When the second joining parts are disposed in a scattered point pattern, the second nonwoven fabric layer can be formed so as to float to the third nonwoven fabric layer in more area, thereby improving the visual shielding property through the nonwoven fabric laminate. It is also preferable that a plurality of the second joining parts are aligned in both one direction and another direction in the nonwoven fabric laminate.

The third joining parts are preferably disposed in a scattered point pattern. When the third joining parts are disposed in a scattered point pattern, hand feeling of the third nonwoven fabric layer side of the nonwoven fabric laminate can be improved. Furthermore, by providing the third joining parts in a scattered point pattern, the fourth nonwoven fabric layer can be formed so as to float to the third nonwoven fabric layer in more area, thereby improving the visual shielding property through the nonwoven fabric laminate. It is also preferable that a plurality of the third joining parts are aligned in both one direction and another direction in the nonwoven fabric laminate.

Both a plurality of the first joining parts and a plurality of the second joining parts (or further a plurality of the third joining parts) are preferably aligned in one direction and another direction in the nonwoven fabric laminate. When the first joining parts and the second joining parts (or further the third joining parts) are provided in this manner, the visual shielding property through the nonwoven fabric laminate is increased to improve the appearance.

The first joining part, the second joining part and the third joining part may have a same shape to each other or may have a different shape from each other. For example, each of the first joining part, the second joining part and the third joining part may be formed in a circular shape, and in this case, it becomes easy to provide a desired physical property isotropically to the nonwoven fabric laminate. Or, the shapes of the first joining part and the third joining part may be determined from the viewpoint of improving the appearance of the nonwoven fabric laminate and the shape of the second joining part may be determined from the viewpoint of increasing the strength of the nonwoven fabric laminate in a desired direction. In this case, the first joining part and the third joining part may have a same shape to each other and the second joining part may have a different shape from the first and third joining parts, or the first joining part, the second joining part and the third joining part may have a different shape from each other. By appropriately setting the shapes of the first to third joining parts, it becomes possible to give a desired physical property to the nonwoven fabric laminate. The first joining parts may be formed in a uniform shape or may be formed in a plurality of various shapes. The same is applied to the second joining parts and the third joining parts.

The second joining part is preferably formed by heat-embossing the second nonwoven fabric layer and the third nonwoven fabric layer. When the second joining part is formed in this manner, the second nonwoven fabric layer and the third nonwoven fabric layer are pressed at the second joining part, thereby increasing strength at the second joining part, and breaking strength of the nonwoven fabric laminate in pulling can be increased.

The first joining part is preferably formed by heat-embossing the first nonwoven fabric layer, the second nonwoven fabric layer and the third nonwoven fabric layer. That is, it is preferred that the first nonwoven fabric layer, the second nonwoven fabric layer and the third nonwoven fabric layer are heat-embossed collectively, whereby the first nonwoven fabric layer, the second nonwoven fabric layer and the third nonwoven fabric layer are thermal-fusion-bonded to each other to form the first joining part. In this case, the second nonwoven fabric layer and the third nonwoven fabric layer are also thermal-fusion-bonded at the same time to form the second joining part, and therefore, the first joining part is formed overlapping with the second joining part. Here, since the second joining parts are provided larger in number than the first joining parts, the first joining parts comes to be formed so as to overlap with a portion of the second joining parts. When the first joining parts and the second joining parts are formed in this manner, integrity of the nonwoven fabric layers constituting the nonwoven fabric laminate is enhanced and strength of the nonwoven fabric laminate is increase.

In the case that the nonwoven fabric laminate comprises the fourth nonwoven fabric layer, the first joining part and the third joining part are preferably formed by heat-embossing the first nonwoven fabric layer, the second nonwoven fabric layer, the third nonwoven fabric layer and the fourth nonwoven fabric layer. That is, it is preferred that the first nonwoven fabric layer, the second nonwoven fabric layer, the third nonwoven fabric layer and the fourth nonwoven fabric layer are heat-embossed collectively, whereby the first nonwoven fabric layer and the second nonwoven fabric layer are thermal-fusion-bonded to each other to form the first joining part as well as the third nonwoven fabric layer and the fourth nonwoven fabric layer are thermal-fusion-bonded to each other to form the third joining part. In this case, the first joining parts and the third joining parts are formed in the same pattern to each other. Further, by heat-embossing the first to fourth nonwoven fabric layers collectively, the second nonwoven fabric layer and the third nonwoven fabric layer are also thermal-fusion-bonded to each other to form the second joining part at the same time, and therefore, the first joining part and the third joining part are formed so as to overlap with the second joining part. On this occasion, since the second joining parts are provided larger in number than the first joining parts and the third joining parts, the first joining parts and the third joining parts come to be formed so as to overlap with a portion of the second joining parts. When the first joining parts, the second joining parts and the third joining parts are formed in this manner, integrity of the nonwoven fabric layers constituting the nonwoven fabric laminate is enhanced and strength of the nonwoven fabric laminate is increase.

Types of a nonwoven fabric constituting each of the nonwoven fabric layer is not particularly limited, and a spunbonded nonwoven fabric, an air-through nonwoven fabric, a point-bonded nonwoven fabric, a meltblown nonwoven fabric, an air-laid nonwoven fabric or the like can be employed. In the case where the nonwoven fabric laminate is applied to, for example, absorbent articles, covers, bags, protective clothing and sheets as described above, the nonwoven fabric laminate preferably has breathability, and in this case, each of the nonwoven fabric layer is preferably made of a spunbonded nonwoven fabric or an air-through nonwoven fabric. When each of the nonwoven fabric layer is made of such nonwoven fabric, breathability of the nonwoven fabric laminate is increased and internal humidity is easily decreased.

As a specific constitution of the nonwoven fabric layers, it is preferred that each of the first nonwoven fabric layer, the second nonwoven fabric layer and the third nonwoven fabric layer is made of a spunbonded nonwoven fabric, for example. When the nonwoven fabric laminate is constituted in this manner, breathability of the nonwoven fabric laminate is increased, and further, since a spunbonded nonwoven fabric is able to be formed relatively thin, interlayer distances between the respective nonwoven fabric layers are easily variously changed, thereby enhancing the visual shielding effect through the nonwoven fabric laminate. In this case, if the nonwoven fabric laminate comprises the fourth nonwoven fabric layer, the fourth nonwoven fabric layer is also preferably made of a spunbonded nonwoven fabric.

As a specific constitution of the nonwoven fabric layers, it is also preferred that the first nonwoven fabric layer is made of an air-through nonwoven fabric and the second and third nonwoven fabric layers are made of a spunbonded nonwoven fabric. An air-through nonwoven fabric is relatively bulky and has a good texture, and hence, when the first nonwoven fabric layer located on an outer surface of the nonwoven fabric laminate is made of an air-through nonwoven fabric, hand feeling of the nonwoven fabric laminate is improved while increasing breathability of the nonwoven fabric laminate. In this case, if the nonwoven fabric laminate comprises the fourth nonwoven fabric layer, the fourth nonwoven fabric layer is preferably made of a spunbonded nonwoven fabric or an air-through nonwoven fabric and is also preferably made of an air-through nonwoven fabric as well as the first nonwoven fabric layer.

A spunbonded nonwoven fabric and an air-through nonwoven fabric can be formed such that fibers constituting the nonwoven fabric orient in one direction. In the case that the first nonwoven fabric layer, the second nonwoven fabric layer and the third nonwoven fabric layer are made of a spunbonded nonwoven fabric or an air-through nonwoven fabric, the first joining part and/or the second joining part preferably has a shape that is shorter in an orientation direction of fibers constituting the nonwoven fabric than in its orthogonal direction. A nonwoven fabric in which constituent fibers are oriented in one direction is formed that breaking strength becomes weak with respect to a direction orthogonal to the orientation direction of the constituent fibers; however, when the first joining part or the second joining part is formed in a shape that is shorter in the fiber orientation direction of the nonwoven fabric (that is, longer in the direction orthogonal to the fiber orientation direction of the nonwoven fabric), the constituent fibers of the nonwoven fabric are firmly joined together at the first joining part and the second joining part, thereby increasing the breaking strength of the nonwoven fabric. As a result, the nonwoven fabric laminate is made hardly to be broken. In the case that the nonwoven fabric laminate comprises the fourth nonwoven fabric layer which is made of a spunbonded nonwoven fabric or an air-through nonwoven fabric, the third joining part preferably has a shape that is shorter in the orientation direction of fibers constituting the nonwoven fabric than in its orthogonal direction. In this case, it is preferable that constituent fibers in all of the nonwoven fabric layers are oriented in the same direction.

The fiber orientation direction of a spunbonded nonwoven fabric or an air-through nonwoven fabric can be determined by observing a surface of the nonwoven fabric with a microscope or the like. A spunbonded nonwoven fabric is formed by, for example, melting a polymer material, extruding from a spinneret to be stretched, and collecting on a conveyor belt or the like to form a web; and on this occasion, the web (fibers) collected on the conveyor belt is arranged along a traveling direction of the conveyor belt. Therefore, in this case, the web (fibers) comes to be oriented in the traveling direction (MD direction) of the conveyor belt. In the air-through nonwoven fabric, the orientation direction of the constituent fibers can be arranged by appropriately setting a collection method of raw short fibers in forming a fiber aggregate or a fiber-opening method in forming a web, upon manufacturing the nonwoven fabric.

Regarding the first joining part and the second joining part, examples of the elongated shape in one direction include an ellipse shape, a rectangle shape, a rhombus shape, a wave shape, a radiation shape and the like. For example, in the case of an elliptical shape, it may be provided in the nonwoven fabric laminate so that the long axis direction corresponds to the one direction.

Fineness of each of the nonwoven fabric layers is not particularly limited; however, it is preferred that fineness of the first nonwoven fabric layer is larger than those of second nonwoven fabric layer and the third nonwoven fabric layer. In the case that the nonwoven fabric laminate comprises the fourth nonwoven fabric layer, it is preferred that fineness of the fourth nonwoven fabric layer is also larger than those of the second nonwoven fabric layer and the third nonwoven fabric layer. When the first nonwoven fabric layer or the fourth nonwoven fabric layer is formed in this manner, void ratio of the first nonwoven fabric layer or the fourth nonwoven fabric layer tends to increase and the first nonwoven fabric layer or the fourth nonwoven fabric layer is formed bulky, resulting in easily improving hand feeling of the nonwoven fabric laminate.

Examples of the nonwoven fabric laminate is described below, referring to FIGS. 1 to 4. However, the nonwoven fabric laminate of the present invention is not limited to the embodiments shown in the drawings.

FIGS. 1 to 3 show perspective views of a nonwoven fabric laminate in which the first nonwoven fabric layer, the second nonwoven fabric layer and the third nonwoven fabric layer are laminated. Nonwoven fabric laminates 1 shown in FIGS. 1 to 3 comprise a first nonwoven fabric layer 2, a second nonwoven fabric layer 3 and a third nonwoven fabric layer 4, and the first nonwoven fabric layer 2, the second nonwoven fabric layer 3 and the third nonwoven fabric layer 4 are laminated in this order. In the nonwoven fabric laminate 1, the first nonwoven fabric layer 2 faces outward. The first nonwoven fabric layer 2 and the second nonwoven fabric layer 3 are joined to each other at first joining parts 6, the second nonwoven fabric layer 3 and the third nonwoven fabric layer 4 are joined to each other at second joining parts 7, and a number of the first joining parts 6 is smaller than that of the second joining parts 7. In FIGS. 1 to 3, the first joining part and the second joining part formed by applying an adhesive are indicated by the reference signs "6A" and "7A", respectively, and the first joining part and the second joining part formed by heat-embossing are indicated by the reference signs "6H" and "7H", respectively.

Since the nonwoven fabric laminate 1 is configured in the above manner, the first joining parts 6 and the second joining parts 7 are formed in a different pattern from each other, and interlayer distances between the respective nonwoven fabric layers are variously changed, whereby a visual shielding property through the nonwoven fabric laminate 1 can be improved. Therefore, when the nonwoven fabric laminate 1 is applied to a conventionally-known nonwoven fabric product, a content and the like covered by the nonwoven fabric laminate 1 can be properly concealed. Further, since the first joining parts 6 formed in the first nonwoven fabric layer 2 which is located on an outer surface of the nonwoven fabric laminate 1 is smaller in number than the second joining parts 7 which join the second nonwoven fabric layer 3 to the third nonwoven fabric layer 4, the appearance of the first nonwoven fabric layer 2 side of the nonwoven fabric laminate 1 can be made neat. Therefore, the appearance of the nonwoven fabric laminate 1 is improved seen from the first nonwoven fabric layer 2 side.

In FIG. 1, the first joining parts 6 and the second joining parts 7 are respectively formed by applying an adhesive, a plurality of the first joining parts 6 are provided so as to be aligned in one direction and another direction in the nonwoven fabric laminate 1, and a plurality of the second joining parts 7 are provided so as to be aligned in one direction and another direction in the nonwoven fabric laminate 1. In the nonwoven fabric laminate 1 shown in FIG.

1, a plurality of the respective joining parts aligned in one direction and another direction can be formed by intermittently applying an adhesive on the nonwoven fabric using a coater (an adhesive coating apparatus) with plural adhesive dispensing nozzles, while moving the nonwoven fabric layer in a direction orthogonal to the array direction of the nozzle.

In FIG. 2, the first joining parts 6 are formed by applying an adhesive, the second joining parts 7 are formed by heat-embossing, a plurality of the first joining parts 6 formed in straight lines extending in one direction are disposed side by side in the nonwoven fabric laminate 1, and a plurality of the second joining parts 7 are provided so as to be aligned in one direction and another direction in the nonwoven fabric laminate 1. In the nonwoven fabric layer 1 shown in FIG. 2, the second joining part 7 can be formed by inserting the second nonwoven fabric layer 3 and the third nonwoven fabric layer 4 in a stacked state between, for example, a heat-embossing roll (that is a roll having a predetermined embossed pattern on its surface and being heatable) and a flat roll to be conveyed. Subsequently, an adhesive is applied continuously in one direction onto the second nonwoven fabric layer 3 integrated with the third nonwoven fabric layer 4, using a coater (an adhesive coating apparatus), to form the first joining part 6, and the first nonwoven fabric layer 2 is stacked thereon, thereby obtaining the nonwoven fabric laminate 1 shown in FIG. 2.

In FIG. 3, the first joining parts 6 and the second joining parts 7 are respectively formed by heat-embossing, a plurality of the second joining parts 7 are provided so as to be aligned in one direction and another direction in the nonwoven fabric laminate 1, and a plurality of the first joining parts 6 are provided so as to be aligned in one direction and another direction in the nonwoven fabric laminate 1 and overlap with a portion of the second joining parts 7. In the nonwoven fabric laminate 1 shown in FIG. 3, a portion of the second joining parts 7 can be formed by inserting the second nonwoven fabric layer 3 and the third nonwoven fabric layer 4 in a stacked state between a heat-embossing roll and a flat roll to be conveyed, and the first joining parts 6 and the other portion of the second joining parts 7, in the state where the first joining parts 6 are overlapped with the second joining parts 7, can be formed by staking the first nonwoven fabric layer 2 thereon and heat-embossing the first nonwoven fabric layer 2, the second nonwoven fabric layer 3 and the third nonwoven fabric layer 4 collectively.

The nonwoven fabric laminate of the present invention is not limited to the embodiments shown in FIGS. 1 to 3, and application patterns of the adhesive, and shapes and patterns of the heat-emboss can be set arbitrarily. Here, the first joining part 6 and the second joining part 7 are preferably provided such that a total area of the first joining parts 6 is smaller than that of the second joining parts 7. In FIGS. 1 to 3, though an area (an average area) of the single first joining part 6 is larger than that of the single second joining part 7, the total area of the second joining parts 7 is larger than that of the first joining parts 6 as a result of the second joining parts 7 being provided larger in number than the first joining parts 6.

FIG. 4 shows a perspective view of a nonwoven fabric laminate 1 in which the first nonwoven fabric layer, the second nonwoven fabric layer, the third nonwoven fabric layer and the fourth nonwoven fabric layer are laminated. FIG. 4 shows an example of the embodiment in which the fourth nonwoven fabric layer is further provided to the nonwoven fabric laminate shown in FIG. 3. In the explanation of the nonwoven fabric laminate shown in FIG. 4, explanations overlapping the above description regarding the FIG. 3 are omitted.

A nonwoven fabric laminate 1 shown in FIG. 4 comprises a first nonwoven fabric layer 2, a second nonwoven fabric layer 3, a third nonwoven fabric layer 4 and a fourth nonwoven fabric layer 5, and the first nonwoven fabric layer 2, the second nonwoven fabric layer 3, the third nonwoven fabric layer 4 and the fourth nonwoven fabric layer 5 are laminated in this order. The first nonwoven fabric layer 2 and the second nonwoven fabric layer 3 are joined to each other at first joining parts 6, the second nonwoven fabric layer 3 and the third nonwoven fabric layer 4 are joined to each other at second joining parts 7, the third nonwoven fabric layer 4 and the fourth nonwoven fabric layer 5 are joined to each other at third joining parts 8, a number of the first joining parts 6 is smaller than that of the second joining parts 7, and a number of the third joining parts 8 is smaller than that of the second joining parts 7. In the nonwoven fabric laminate 1 shown in FIG. 4, since the first joining parts 6 and the third joining parts 8 are formed in a different pattern from the second joining parts 7, interlayer distances between the respective nonwoven fabric layers are variously changed, whereby a visual shielding property through the nonwoven fabric laminate 1 can be improved. Further, since the first joining parts 6 formed in the first nonwoven fabric layer 2 and the third joining parts 8 formed in the fourth nonwoven fabric layer 5, that are located on outer surfaces of the nonwoven fabric laminate 1, are smaller in number than the second joining parts 7 which join the second nonwoven fabric layer 3 to the third nonwoven fabric layer 4, the appearance of both the first nonwoven fabric layer 2 side and the fourth nonwoven fabric layer 5 side of the nonwoven fabric laminate 1 can be made neat. Therefore, the appearance of the nonwoven fabric laminate 1 is improved.

In the nonwoven fabric laminate 1 shown in FIG. 4, the first joining parts 6, the second joining parts 7 and the third joining parts 8 are respectively formed by heat-embossing. In the nonwoven fabric laminate 1 shown in FIG. 4, a portion of the second joining parts 8 can be formed by inserting the second nonwoven fabric layer 3 and the third nonwoven fabric layer 4 in a stacked state between, for example, a heat-embossing roll and a flat roll to be conveyed, and the other portion of the second joining parts 7 in conjunction with the first joining parts 6 and the third joining parts 8, in the state where the first joining parts 6 and the third joining parts 8 are overlapped with the second joining parts 7, can be formed by laminating the first nonwoven fabric layer 2 thereon and the fourth nonwoven fabric layer 5 thereunder and heat-embossing the first nonwoven fabric layer 2, the second nonwoven fabric layer 3, the third nonwoven fabric layer 4 and the fourth nonwoven fabric layer 5 collectively.

[Absorbent Article]

Next, an absorbent article of the present invention is explained. An absorbent article of the present invention comprises an exterior sheet formed of the nonwoven fabric laminate of the present invention. By employing the nonwoven fabric laminate of the present invention for the exterior sheet of an absorbent article, a visual shielding property of the exterior sheet is enhanced and the appearance thereof is improved. Examples of the absorbent article include a disposable diaper, an incontinence pad (including a light incontinence pad) and a sanitary napkin.

The absorbent article has a skin-facing side and an outer side with respect to a thickness direction of the absorbent article. A skin-facing side of the absorbent article means a side close to wearer's skin in wearing the absorbent article and an outer side of the absorbent article means a side opposite to a wearer in wearing the absorbent article.

The exterior sheet is located on an outer side of the absorbent article. For example, the absorbent article comprises a top sheet, a back sheet and an absorbent core provided therebetween, and in the case where the back sheet is disposed on an outer side of the absorbent article, the back sheet corresponds to the exterior sheet. In the case where the absorbent article is a pants-type disposable diaper, the pants-type disposable diaper may be formed such that an absorbent body comprising a top sheet, a back sheet and an absorbent core provided therebetween is disposed on a skin-facing side of a pants member that is formed in a pants shape; and in this case, at least a portion of the pants member may be composed of the exterior sheet. As just described, it is preferred that the exterior sheet is provided so as to constitute the outer side the absorbent article.

A shape of the absorbent article is not particularly limited. In the case where the absorbent article is an incontinence pad, examples of the shape of the absorbent article include a substantially rectangular shape, an hourglass shape, a center nipped-in gourd shape, a battledore shape and others.

In the case where the absorbent article is a disposable diaper, the absorbent article has, for example, a front part, a rear part, and a crotch part positioned therebetween and provided with an absorbent core. The disposable diaper may be an open-type (tape-type) disposable diaper that is provided with a pair of fastening members on left and right sides of a rear part and is formed into a pants shape by using the fastening members in wearing, or the disposable diaper may be a pants-type disposable diaper that is formed in a pants shape and has a waist opening and a pair of leg openings. The disposable diaper may comprise, for example, an exterior member having a front part, a rear part and a crotch part positioned therebetween and an absorbent body comprising a top sheet, a back sheet and an absorbent core provided therebetween, wherein the absorbent body is disposed on a skin-facing side of the exterior member. Or, the disposable diaper may be formed such that a laminate comprising a top sheet, a back sheet and an absorbent core provided therebetween has a front part, a rear part and a crotch part positioned therebetween. Here, the front part means a part applied to an abdomen side of the wearer, the rear part means a part applied to a back side of the wearer, and the crotch part means a part positioned between the front part and the rear part and applied to a crotch of the wearer, in wearing the disposable diaper.

The exterior sheet is composed of the nonwoven fabric laminate of the present invention. In the nonwoven fabric laminate of the present invention, the first nonwoven fabric layer is preferably faces outward; and hence, in the case of applying to the exterior sheet of the absorbent article, it is preferred that the first nonwoven fabric layer is located on an outer side of the absorbent article. Thus, the exterior sheet comprises the first nonwoven fabric layer, the second nonwoven fabric layer and the third nonwoven fabric layer from the outer side of the absorbent article, the first nonwoven fabric layer and the second nonwoven fabric layer are joined to each other at the first joining parts, and the second nonwoven fabric layer and the third nonwoven fabric layer are joined to each other at the second joining parts. And, a number of the first joining parts is smaller than that of the second joining parts. That is, the second joining parts are provided in high density in a numerical criterion than the first joining parts. Since the exterior sheet is configured in this manner, the first joining parts and the second joining parts are provided in a different pattern from each other, an interlayer distance between the first nonwoven fabric layer and the second nonwoven fabric layer and an interlayer distance between the second nonwoven fabric layer and the third nonwoven fabric layer are variously changed, that makes degree of transmission or diffusion of light through the exterior sheet uneven properly, whereby the visual shielding property through the exterior sheet can be increased. For example, in the case that an elastic member is disposed to the skin-facing side of the exterior sheet, the elastic member becomes hardly seen from the outside of the absorbent article, thereby improving the appearance of the absorbent article. Or, in the case that an absorbent core disposed to the skin-facing side of the exterior sheet is colored by absorbing excrement, the absorbent core can be made less obvious seen from the outside of the absorbent article, thereby improving the appearance of the absorbent article.

Further, since the first joining parts formed in the first nonwoven fabric layer which is located on an outer side of the exterior sheet are provided smaller in number than the second joining parts which join the second nonwoven fabric layer with the third nonwoven fabric layer, the appearance of the exterior sheet can be made neat. Furthermore, though the first joining parts and the second joining parts are formed by applying an adhesive to the nonwoven fabric layer, thermal-fusion-bonding the nonwoven fabric layers to each other, or the like, and such formed joining parts tend to be hardened to deteriorate the hand feeling, decreasing the number of the first joining parts formed in the first nonwoven fabric layer enables improving the hand feeling of the exterior sheet.

The exterior sheet is formed by laminating the first nonwoven fabric layer, the second nonwoven fabric layer and the third nonwoven fabric layer and is handled as a single sheet member; and thus, no elastic member is provided between the respective nonwoven fabric layers constituting the exterior sheet (that is, between the first nonwoven fabric layer and the second nonwoven fabric layer, and between the second nonwoven fabric layer and the third nonwoven fabric layer). In the exterior sheet, another layer may be provided on the outer side of the first nonwoven fabric layer or the skin-facing side of the third nonwoven fabric layer; however, the exterior sheet preferably does not comprise so many layers in view of easily ensuring flexibility and breathability of the exterior sheet and preferably consists of the first nonwoven fabric layer, the second nonwoven fabric layer and the third nonwoven fabric layer. Preferred embodiments relating to the arrangement patterns, shapes, sizes and the like of each of the joining parts are the same as described above.

Types of a nonwoven fabric constituting each of the nonwoven fabric layer is not particularly limited, and a spunbonded nonwoven fabric, an air-through nonwoven fabric, a point-bonded nonwoven fabric, a meltblown nonwoven fabric, an air-laid nonwoven fabric or the like can be employed. Here, the exterior sheet is located on the outer side of the absorbent article and preferably has breathability, and in this respect, each of the nonwoven fabric layers constituting the exterior sheet is preferably made of a spunbonded nonwoven fabric or an air-through nonwoven fabric. When each of the nonwoven fabric layers of the exterior sheet is made of such nonwoven fabric, breathability of the exterior sheet is increased and internal humidity is easily decreased in wearing the absorbent article.

As a specific constitution of the first nonwoven fabric layer, the second nonwoven fabric layer and the third nonwoven fabric layer constituting the exterior sheet, it is preferred that each of the first nonwoven fabric layer, the second nonwoven fabric layer and the third nonwoven fabric layer is made of a spunbonded nonwoven fabric. When the exterior sheet is constituted in this manner, breathability of the exterior sheet is increased, and further, since a spunbonded nonwoven fabric is able to be formed relatively thin, distances between the respective nonwoven fabric layers are easily randomly changed, thereby increasing the visual shielding effect of the exterior sheet.

Regarding the first nonwoven fabric layer, the second nonwoven fabric layer and the third nonwoven fabric layer, it is also preferred that the first nonwoven fabric layer is made of an air-through nonwoven fabric and the second and third nonwoven fabric layers are made of a spunbonded nonwoven fabric. An air-through nonwoven fabric is relatively bulky and has a good texture, and hence, when the first nonwoven fabric layer located on the outer side of the exterior sheet is made of an air-through nonwoven fabric, hand feeling of the exterior sheet is improved while increasing breathability of the exterior sheet.

In the case that an elastic member is disposed to the skin-facing side of the exterior sheet, a visual shielding property of the exterior sheet can be increased by providing the first joining part as follows, whereby the elastic member becomes hardly seen from the outside of the exterior sheet. That is, it is preferred that an elastic member is disposed to the skin-facing side of the exterior sheet and the first joining part has a shape that is shorter in an extending direction of the elastic member than in an orthogonal direction thereof. When the first joining part is provided in this manner, many wrinkles extending in the direction orthogonal to the extending direction of the elastic member are easily formed in the exterior sheet, and the elastic member becomes hardly seen from the outside of the exterior sheet. Specifically, in the present invention, two kinds of joining parts, the first joining part and the second joining part, are formed in the exterior sheet as described above, and therefore, a large number of fine wrinkles are formed in the exterior sheet and distances between the respective nonwoven fabric layers are randomly changed, thereby increasing the visual shielding effect of the exterior sheet.

In the case that an elastic member is disposed to the skin-facing side of the exterior sheet, it is also preferable that a plurality of the first joining parts are aligned in the extending direction of the elastic member and an orthogonal direction thereof, and a distance between the first joining parts in the extending direction of the elastic member is wider than that in the orthogonal direction thereof. Also in the case that the first joining part is provided in this manner, many wrinkles extending in the direction orthogonal to the extending direction of the elastic member tend to be formed in the exterior sheet when the elastic member disposed to the skin-facing side of the exterior sheet contracts, and as a result, the elastic member becomes hardly seen from the outside of the exterior sheet to improve the appearance of the absorbent article.

In the case that the elastic member is disposed to the skin-facing side of the exterior sheet, the elastic member is preferably adhered to the skin-facing side of the exterior sheet. In addition, the first joining part is preferably provided at a region where the elastic member is disposed in the exterior sheet.

Next, examples of the absorbent article of the present invention is explained, referring to drawings. However, the absorbent article of the present invention is not limited to the embodiments shown in the drawings.

FIGS. 5 and 6 show an example of the absorbent article of the present invention that is applied to an incontinence pad. FIG. 5 shows a plan view of a skin-facing side of an incontinence pad, and FIG. 6 shows a cross-sectional view along a line VI-VI of the incontinence pad shown in FIG. 5. In the drawings, an arrow x represents a width direction and an arrow y represents a longitudinal direction, and a direction orthogonal to the arrows x and y represents a thickness direction z. The longitudinal direction y corresponds to a direction extending in a front-rear direction at a crotch of a wearer when the wearer wears the absorbent article, and the width direction x means a direction orthogonal to the longitudinal direction y on the same plane as the absorbent article.

An absorbent article (an incontinence pad) 11 comprises a top sheet 12, a back sheet 13 and an absorbent core 14 provided therebetween. The top sheet 12 is located on a skin-facing side of the absorbent article 11 and allows urine and the like excreted from a wearer to permeate through. The urine and the like which has passed through the top sheet 12 is accommodated in the absorbent core 14. The back sheet 13 is located on an outer side of the absorbent article 11 and prevents the excrement from permeating outside. In the absorbent article 11, the absorbent core 14 is formed in an hourglass shape.

In the absorbent article 11, it is preferred that side sheets 15 extending in the longitudinal direction y are disposed on both sides of the top sheet 12 in the width direction x. The side sheet 15 is provided with a rising elastic member 16 at an inner part thereof in the width direction x, and the inner part of the side sheet 15 rises toward wearer's skin by contractive force of the rising elastic member 16 in using the absorbent article 11, thereby preventing leakage of excrement such as urine and the like.

In the absorbent article 11, the nonwoven fabric laminate of the present invention can be used for the back sheet 13 as the exterior sheet. For example, in the case of using the above-described nonwoven fabric laminate 1, the nonwoven fabric laminate 1 may be disposed such that the first nonwoven fabric layer 2 is located on the outer side of the absorbent article 11. By applying the nonwoven fabric laminate of the present invention to the back sheet 13 as the exterior sheet, the appearance of the absorbent article 11 seen from the back sheet 13 side is enhanced, for example in the case of using the absorbent article 11 to be attached to an inner side of an underwear (pants). Or, the nonwoven fabric laminate of the present invention may be further provided on the outer side of the back sheet 13 as the exterior sheet.

An another example of the absorbent article of the present invention is explained. FIGS. 7 to 9 show an example of the absorbent article that is applied to a pants-type disposable diaper. FIG. 7 shows a perspective view of a pants-type disposable diaper, FIG. 8 shows a plan view of the pants-type disposable diaper shown in FIG. 7 in a developed state where a front part and a rear part are disjoined, and FIG. 9 shows a cross-sectional view along a line IX-IX of the pants-type disposable diaper shown in FIG. 8.

An absorbent article (a pants-type disposable diaper) 21 comprises a pants member 24 having a waist opening 22 and a pair of leg openings 23, and an absorbent body 27 disposed on a skin-facing side of the pants member 24. The pants member 24 has a front part P, a rear part Q and a crotch part R positioned therebetween, and formed into a pants shape by joining the front part P and the rear part Q. In the absorbent article (a pants-type disposable diaper) 21, the front part P and the rear part Q constitute a body circumference part of the diaper, and a part between an edge of the waist opening 22 and an edge of the leg opening 23 corresponds to the body circumference part of the diaper.

In the absorbent article 21, the nonwoven fabric laminate of the present invention can be used for a sheet member located on the outer side of the pants member 24. In FIGS. 7 to 9, the nonwoven fabric laminate of the present invention is used for an exterior sheet 25 located on the outer side of the pants member 24, and an inner sheet 26 is laminated on the skin-facing side of the exterior sheet 25. By providing the exterior sheet 25 located on the outer side of the absorbent article 21, the appearance of the absorbent article 21 can be improved.

The absorbent body 27 is disposed on the skin-facing side of the pants member 24 at least at the crotch part R, and comprises a top sheet 28, a back sheet 29 and an absorbent core 30 provided therebetween (see FIGS. 8 and 9). In the absorbent article 21, the absorbent body 27 and the absorbent core 30 are formed in a substantially rectangular shape. The back sheet 29 is folded along an edge of the absorbent core 30 in the width direction x and joined to the top sheet 28.

The absorbent body 27 is provided with rising flaps 31 on both sides thereof in the width direction x (see FIGS. 8 and 9). The rising flap 31 enables preventing leakage of excrement such as urine and the like. The rising flap 31 is preferably liquid-impermeable. The rising flap 31 is provided with a rising elastic member 32 at an upper end part thereof in its standing state (an end part of a wearer's side), and the rising flap 31 is promoted to stand by contractive force of the rising elastic member 32.

A plurality of waist elastic members 33 are disposed along an edge of the waist opening 22 at an end part, with respect to the longitudinal direction y, of the pants member 24. A waist-gather around a wearer's waist is formed by the waist elastic member 33, thereby preventing excrement such as urine and the like from leaking from a back side or an abdomen side.

A plurality of body elastic members 34 extending in the width direction x are disposed at the front part P and the rear part Q of the pants member 24. The body elastic members 34 are arranged at wider intervals than the waist elastic member 33. The body elastic member 34 functions to improve fittability around a wearer's body.

Leg elastic members 35, 36 are disposed in the pants member 24 along an edge of the leg opening 23. The leg elastic member consists of a front leg elastic member 35 disposed along a front side of the edge of the leg opening 23 and a rear leg elastic member 36 disposed along a rear side of the edge of the leg opening 23; and by the front leg elastic member 35 and the rear leg elastic member 36, the leg elastic member is disposed along almost the entire circumference of the edge of the leg opening 23. Leg-gathers around wearer's legs formed by the leg elastic members 35, 36 prevents excrement such as urine and the like from leaking from a crotch.

The waist elastic member 33, the body elastic member 34 and the leg elastic members 35, 36 may be disposed between the exterior sheet 25 and the inner sheet 26. Each of the elastic member is preferably bonded to the exterior sheet 25 and/or the inner sheet 26 in the stretched state. The exterior sheet 25 may be folded back at the edge of the waist opening 22 of the pants member 24 toward the inner sheet 26, and the waist elastic member 33 may be interposed between the folded and unfolded parts of the exterior sheet 25 and bonded to the exterior sheet 25.

In the case that an elastic member extending in the width direction x, such as the waist elastic member 33 and the body elastic member 34, is disposed between the exterior sheet 25 and the inner sheet 26, the first joining part provided in the exterior sheet 25 is preferably formed so as to have a shape that is longer in the longitudinal direction y than in the width direction x at the body circumference part of the diaper (that is, the front part P and/or the rear part Q). When the first joining part is provided in this manner, many wrinkles extending in the longitudinal direction y are formed in the exterior sheet 25, and the waist elastic member 33 or the body elastic member 34 can be made hardly to be seen from the outside of the exterior sheet 25. Specifically, in the exterior sheet 25, two kinds of joining parts, the first joining part and the second joining part, are formed, and therefore, a large number of fine wrinkles can be formed in the exterior sheet 25, thereby increasing the visual shielding effect of the exterior sheet 25.

It is also preferable that a plurality of the first joining parts are aligned in the width direction x and the longitudinal direction y in the body circumference part of the diaper, and a distance between the first joining parts in the width direction x is wider than that in the longitudinal direction y. Also by providing the first joining part in this manner, many wrinkles extending in the longitudinal direction y are formed in the exterior sheet 25 when the elastic members 33, 34 contract in the width direction x, and as a result, the elastic members 33, 34 can be made hardly to be seen from the outside of the exterior sheet 25.

Materials of members constituting the absorbent article of the present invention are explained. The top sheet is a sheet which is located on a wearer's side in wearing the absorbent article and preferably liquid-permeable. Examples of the top sheet include, for example, a nonwoven fabric formed from hydrophilic fibers such as cellulose, rayon and cotton; and a nonwoven fabric which is formed from hydrophobic fibers such as polyolefin (e.g., polypropylene, polyethylene), polyester (e.g., PET) and polyamide (e.g., nylon), and in which the hydrophobic fibers are hydrophilized with a surfactant on the surface thereof. As the top sheet, a woven fabric, a knitted fabric, a plastic film having pores may be also used.

The back sheet is a sheet which is located on an opposite side of the wearer, that is an exterior side, in wearing the absorbent article and preferably liquid-impermeable. Examples of the back sheet include, for example, a nonwoven fabric formed from hydrophobic fibers such as polyolefin (e.g., polypropylene, polyethylene), polyester (e.g., PET) and polyamide (e.g., nylon), and a plastic film. As the back sheet, a laminate of a nonwoven fabric and a plastic film may be also used. In the present invention, the meaning of "liquid-impermeable" includes water-repellent.

The pants member (the inner sheet and the exterior sheet) may be liquid-permeable or liquid-impermeable, and a sheet material usable for the top sheet or the back sheet can be used.

In the case of using a nonwoven fabric for the above sheet material, a spunbonded nonwoven fabric, an air-through nonwoven fabric, a point-bonded nonwoven fabric, a melt-blown nonwoven fabric, an air-laid nonwoven fabric, an SMS nonwoven fabric or the like is preferably used as the nonwoven fabric. In the case where the nonwoven fabric layers are joined to each other by heat-embossing in the exterior sheet (the nonwoven fabric laminate), they preferably contain thermal welding fibers such as polyolefin (e.g., polypropylene, polyethylene), polyester (e.g., PET) and polyamide (e.g., nylon).

The absorbent core is not particularly restricted as long as it absorbs excrement such as urine and the like. As the absorbent core, a clump of an absorbent material, which is formed into a predefined shape, may be used. The absorbent core may be wrapped with a sheet member such as paper (e.g., a tissue paper and a thin paper) and a liquid-permeable nonwoven fabric. Examples of the absorbent material contained in the absorbent core include, for example, a hydrophilic fiber such as a cellulose fiber (e.g., a crushed pulp fiber) and an absorbent polymer such as polyacrylic absorbent polymer, polyasparaginic absorbent polymer, cellulosic absorbent polymer, and stark-acrylonitrile absorbent polymer. The absorbent material may contain a thermal welding fiber. The welding fiber may be hydrophilized with a surfactant or the like to increase affinity with a bodily fluid such as urine.

The absorbent material preferably contains a hydrophilic fiber in view of increasing absorption speed of urine or the like. In addition, in view of enhancing absorption capacity, the absorbent material preferably contains an absorbent polymer. Therefore, the absorbent core preferably contains both a hydrophilic fiber (especially a pulp fiber) and an absorbent polymer. In this case, the absorbent material is preferably obtained by mixing an absorbent polymer with a hydrophilic fiber assembly, or dispersing an absorbent polymer on a hydrophilic fiber assembly, for example.

The absorbent core may be a sheet-shaped absorbent body. Examples of the sheet-shaped absorbent body include an object which is formed to contain an absorbent polymer but not contain a pulp fiber between nonwoven fabrics. The sheet-shaped absorbent body formed in this manner enables high absorption capacity since it contains an absorbent polymer between nonwoven fabrics. In addition, since the sheet-shaped absorbent body does not contain a pulp fiber between nonwoven fabrics, it can be formed thin without being bulky.

As the sheet-shaped absorbent body, an absorbent fiber may be used for the absorbent material. Also in this case, the sheet-shaped absorbent body is formed thin without being bulky. Examples of the absorbent fiber include a fiber having a protonated carboxyl group or a carboxylate group. The absorbent fiber can be obtained by, for example, hydrolyzing an acrylic fiber, thereby converting a nitrile group contained in the acrylic fiber to a carboxylic group, as disclosed in Japanese Examined Patent Application Publication No. S52-42916. The carboxyl group contained in the absorbent fiber is preferably forms an alkaline metal salt or an ammonium salt. The absorbent fiber also can be prepared by immersing a hydrophilic fiber in acrylic acid to deposit acrylic acid on the surface of the fiber.

This application claims priority to Japanese Patent Application No. 2013-203774, filed on Sep. 30, 2013, the entire contents of which are incorporated by reference herein.

REFERENCE SIGNS LIST

1: a nonwoven fabric laminate
2: a first nonwoven fabric layer
3: a second nonwoven fabric layer
4: a third nonwoven fabric layer
5: a fourth nonwoven fabric layer
6: a first joining part
7: a second joining part
11, 21: an absorbent article
12, 28: a top sheet
13, 29: a back sheet
14, 30: an absorbent core
24: a pants member
25: an exterior sheet
26: an inner sheet
33: a waist elastic member
34: a body elastic member

The invention claimed is:

1. An absorbent article comprising an exterior sheet formed of a plurality of nonwoven fabric layers, wherein
the exterior sheet is located on an outer side of the absorbent article and has a first nonwoven fabric layer, a second nonwoven fabric layer and a third nonwoven fabric layer from the outer side of the absorbent article,
the first nonwoven fabric layer and the second nonwoven fabric layer are joined to each other at first joining parts,
the second nonwoven fabric layer and the third nonwoven fabric layer are joined to each other at second joining parts,
a number of the first joining parts is smaller than that of the second joining parts, and
no elastic member is provided between the first nonwoven fabric layer and the second nonwoven fabric layer and between the second nonwoven fabric layer and the third nonwoven fabric layer.

2. The absorbent article according to claim 1, wherein a total area of the first joining parts is smaller than that of the second joining parts.

3. The absorbent article according to claim 1, wherein both a plurality of the first joining parts and a plurality of the second joining parts are aligned in one direction and another direction in the exterior sheet.

4. The absorbent article according to claim 1, wherein each of the first nonwoven fabric layer, the second nonwoven fabric layer and the third nonwoven fabric layer is made of a spunbonded nonwoven fabric or an air-through nonwoven fabric.

5. The absorbent article according to claim 4, wherein the first joining part and/or the second joining part has a shape that is shorter in an orientation direction of fibers constituting the nonwoven fabric than in its orthogonal direction.

6. The absorbent article according to claim 1, wherein
an elastic member is disposed to a skin-facing side of the exterior sheet, and
the first joining part has a shape that is shorter in an extending direction of the elastic member than in an orthogonal direction thereof.

7. The absorbent article according to claim 1, wherein
an elastic member is disposed to a skin-facing side of the exterior sheet, and
a plurality of the first joining parts are aligned in an extending direction of the elastic member and an orthogonal direction thereof, and a distance between the first joining parts in the extending direction is wider than that in the orthogonal direction.

8. The absorbent article according to claim 1, wherein
the absorbent article is a pants-type disposable diaper,
an elastic member extending in a width direction of the diaper is disposed at a body circumference part of the diaper between the exterior sheet and an inner sheet provided on a skin-facing side of the exterior sheet, and
the first joining part has a shape that is longer in a longitudinal direction of the diaper than in the width direction of the diaper.

9. The absorbent article according to claim 1, wherein
the absorbent article is a pants-type disposable diaper,
an elastic member extending in a width direction of the diaper is disposed at a body circumference part of the diaper between the exterior sheet and an inner sheet provided on a skin-facing side of the exterior sheet, and a plurality of the first joining parts are aligned in a longitudinal direction of the diaper and the width direction of the diaper, and a distance between the first joining parts in the width direction of the diaper is wider than that in the longitudinal direction of the diaper.

10. A nonwoven fabric laminate in which a first nonwoven fabric layer, a second nonwoven fabric layer and a third nonwoven fabric layer are laminated in this order, wherein the first nonwoven fabric layer and the second nonwoven fabric layer are joined to each other at first joining parts, the second nonwoven fabric layer and the third nonwoven fabric layer are joined to each other at second joining parts, a number of the first joining parts is smaller than that of the second joining parts, and no elastic member is provided between the first nonwoven fabric layer and the second nonwoven fabric layer and between the second nonwoven fabric layer and the third nonwoven fabric layer.

11. The nonwoven fabric laminate according to claim 10, wherein a total area of the first joining parts is smaller than that of the second joining parts.

12. The nonwoven fabric laminate according to claim 10, wherein both a plurality of the first joining parts and a plurality of the second joining parts are aligned in one direction and another direction in the nonwoven fabric laminate.

13. The nonwoven fabric laminate according to claim 10, wherein each of the first nonwoven fabric layer, the second nonwoven fabric layer and the third nonwoven fabric layer is made of a spunbonded nonwoven fabric or an air-through nonwoven fabric.

14. The nonwoven fabric laminate according to claim 13, wherein the first joining part and/or the second joining part has a shape that is shorter in an orientation direction of fibers constituting the nonwoven fabric than in its orthogonal direction.

* * * * *